United States Patent
Okamoto et al.

(10) Patent No.: US 7,953,263 B2
(45) Date of Patent: May 31, 2011

(54) X-RAY CT APPARATUS AND IMAGE PROCESSING APPARATUS

(75) Inventors: Yosuke Okamoto, Yokohama (JP); Satoru Nakanishi, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1013 days.

(21) Appl. No.: 11/753,783

(22) Filed: May 25, 2007

(65) Prior Publication Data

US 2007/0230653 A1    Oct. 4, 2007

Related U.S. Application Data

(63) Continuation of application No. PCT/JP2005/021588, filed on Nov. 24, 2005.

(30) Foreign Application Priority Data

Nov. 26, 2004   (JP) .................. 2004-342272
Nov. 26, 2004   (JP) .................. 2004-342273

(51) Int. Cl.
  *G06K 9/00*   (2006.01)
  *A61B 6/00*   (2006.01)
  *H05G 1/64*   (2006.01)
(52) U.S. Cl. ................. 382/128; 378/4; 378/98.11
(58) Field of Classification Search .............. 382/100, 382/128–134; 378/4, 8, 98.11; 128/920; 600/1, 300; 606/1
See application file for complete search history.

(56) References Cited

U.S. PATENT DOCUMENTS

| 6,266,388 | B1 | 7/2001 | Hsieh | |
| 6,920,238 | B1* | 7/2005 | Chen et al. | 382/128 |
| 6,922,462 | B2 | 7/2005 | Acharya et al. | |
| 7,236,618 | B1* | 6/2007 | Chui et al. | 382/128 |
| 7,783,096 | B2* | 8/2010 | Chen et al. | 382/128 |
| 2004/0022359 | A1 | 2/2004 | Acharya et al. | |
| 2007/0286330 | A1* | 12/2007 | Boing et al. | 378/4 |

FOREIGN PATENT DOCUMENTS

| CN | 1547161 A | 11/2004 |
| JP | 10-40372 | 2/1998 |
| JP | 2001-137228 A | 5/2001 |
| JP | 2001-190550 A | 7/2001 |
| JP | 2004-65975 A | 3/2004 |

(Continued)

OTHER PUBLICATIONS

Translation for application JP 2000-003651 filed on Dec. 1, 2000, publication 2001-190550, Arai Yoshinori< Suzuki Masakazi, Univ. Nihon. pp. 1-15.*

(Continued)

*Primary Examiner* — Samir A Ahmed
*Assistant Examiner* — Mehdi Rashidian
(74) *Attorney, Agent, or Firm* — Oblon, Spivak, McClelland, Maier & Neustadt, L.L.P.

(57) ABSTRACT

An X-ray CT apparatus includes a unit which extracts a high-contrast region of comparatively high X-ray attenuation coefficient from an image, units which generate an unsharp image concerning the high-contrast region, on the basis of the position of the extracted high-contrast region and a point spread function peculiar to the apparatus, and a unit which subtracts the unsharp image from the original image in order to generate a low-contrast image concerning a low-contrast region of comparatively low X-ray attenuation coefficient.

22 Claims, 8 Drawing Sheets

FOREIGN PATENT DOCUMENTS

JP         2004-174218 A     6/2004

OTHER PUBLICATIONS

Marcel Van Straten, et al., "Removal of arterial wall calcifications in CT angiography by local subtraction", Medical Physics, vol. 30, No. 5, XP012012060, May 1, 2003, pp. 761-770.

Jiang Hsieh, "A Practical Cone Beam Artifact Correction Algorithm", IEEE Nuclear Science Symposium Conference Record 2000 Lyon, France, vol. 2, XP010557010, Oct. 15, 2000, pp. 15-71-15-74.

Marcel Van Straten, et al., "Removal of bone in CT angiography of the cervical arteries by piecewise matched mask bone elimination", Medical Physics, vol. 31, No. 10, XP012075063, Oct. 1, 2004, pp. 2924-2933.

Abdalmajeid M. Alyassin, et al., "Semi-automatic bone removal technique from CT angiography data", Proceedings of SPIE, vol. 4322, XP002335330, Jan. 1, 2001, pp. 1273-1283.

Muhammad Bilal Ahmad, et al., "Local Threshold and Boolean Function Based Edge Detection", IEEE Transactions on Consumer Electronics, IEEE Service Center, New York, NY, US, vol. 45, No. 3, XP011083788, Aug. 1, 1999, pp. 674-679.

Øivind Due Trier, et al., "Evaluation of Binarization Methods for Utility Map Images", IEEE Proceedings of the International Conference on Image Procesing (ICIP) Austin, vol. 2, Nov. 13, 1994, pp. 1046-1050.

\* cited by examiner

US 7,953,263 B2

X-RAY CT APPARATUS AND IMAGE PROCESSING APPARATUS

CROSS-REFERENCE TO RELATED APPLICATIONS

This is a Continuation Application of PCT application No. PCT/JP2005/021588, filed Nov. 24, 2005, which was published under PCT Article 21(2) in Japanese.

This application is based upon and claims the benefit of priority from prior Japanese Patent Applications No. 2004-342272, filed Nov. 26, 2004; and No. 2004-342273, filed Nov. 26, 2004, the entire contents of both of which are incorporated herein by reference.

BACKGROUND OF THE INVENTION

1. Field of the Invention

The present invention relates to an X-ray CT apparatus and an image processing apparatus which generate an image within a patient, on the basis of projection data obtained by irradiating the patient with X-rays.

2. Description of the Related Art

The progress of X-ray CT apparatuses is remarkable, and in compliance with the eager desire of medical treatment sites to radiograph a patient at a higher precision (higher resolution) and in a wider range, a multislice X-ray CT apparatus has been developed and has come into considerably wide use in recent years. The multislice X-ray CT apparatus is a scanner including an X-ray source which irradiates the patient with fan beam X-rays having a spread width in a slice direction (the lengthwise direction of a patient couch), and a two-dimensional detector of a structure in which a plurality of detection element rows (of 4 rows, 8 rows, 16 rows, or the like) are arrayed in the slice direction, wherein the X-rays are moved by multiscan or helical scan. Thus, as compared with a single-slice X-ray CT apparatus, the multislice X-ray CT apparatus can obtain volume data over a wider range within the patient, at a higher precision and in a shorter time.

In a case where a blood vessel in a CT image generated by such an X-ray CT apparatus has a high-contrast substance (a substance having a high X-ray attenuation coefficient) nearby, the situation of a cavity in the blood vessel becomes unclear under the influence of unsharpness ascribable to the substance. Heretofore, as a method for improving the image quality of a noted region without being influenced by a high-contrast region, there has been known a method wherein image processing is executed after the CT number of the high-contrast region is set at a suitable value adjusted to the CT number of the surroundings, whereupon the value of the high-contrast region is restored. With this method, however, it has been impossible to favorably eliminate the unsharpness of the surroundings of the high-contrast region (refer to JP-A-10-40372).

BRIEF SUMMARY OF THE INVENTION

An object of the present invention is to relieve unsharpness which appears in the surroundings of an object of high X-ray attenuation coefficient in case of displaying the X-ray absorption distribution image of the interior of a patient as has been obtained by an X-ray CT apparatus.

The first aspect of the invention provides, in an X-ray CT apparatus wherein projection data on a patient are acquired, and an image within the patient is reconstructed on the basis of the acquired projection data, an X-ray CT apparatus comprising a unit which is configured so as to extract a high-contrast region of comparatively high X-ray attenuation coefficient from the image; a unit which is configured so as to generate an unsharp image concerning the high-contrast region, on the basis of a position of the extracted high-contrast region and a point spread function peculiar to the apparatus; and a unit which is configured so as to subtract the unsharp image from the first-mentioned image in order to generate a low-contrast image concerning a low-contrast region of comparatively low X-ray attenuation coefficient.

The second aspect of the invention provides, in an X-ray CT apparatus wherein projection data on a patient are acquired, and an image within the patient is reconstructed on the basis of the acquired projection data, an X-ray CT apparatus comprising a unit which subtracts an unsharp image concerning a region of comparatively high X-ray attenuation coefficient as is contained in the first-mentioned image, from the first-mentioned image in order to generate a low-contrast image concerning a region of comparatively low X-ray attenuation coefficient; a unit which classifies the low-contrast image into a plurality of regions in accordance with CT numbers; and a unit which replaces pixel values of the low-contrast image with values that are respectively peculiar to the plurality of classified regions.

The third aspect of the invention provides, in an X-ray CT apparatus wherein projection data on a patient are acquired, and an image within the patient is reconstructed on the basis of the acquired projection data, an X-ray CT apparatus comprising a unit which extracts a plurality of included region candidates of different sizes in succession, from an image on the basis of a plurality of threshold values; a unit which computes respective gravitational centers of the plurality of extracted regions; and a unit which selects a specified region from the plurality of extracted region candidates on the basis of distances between the gravitational centers.

DETAILED DESCRIPTION OF THE INVENTION

First Embodiment

Now, the first embodiment of the present invention will be described.

Figure 1:
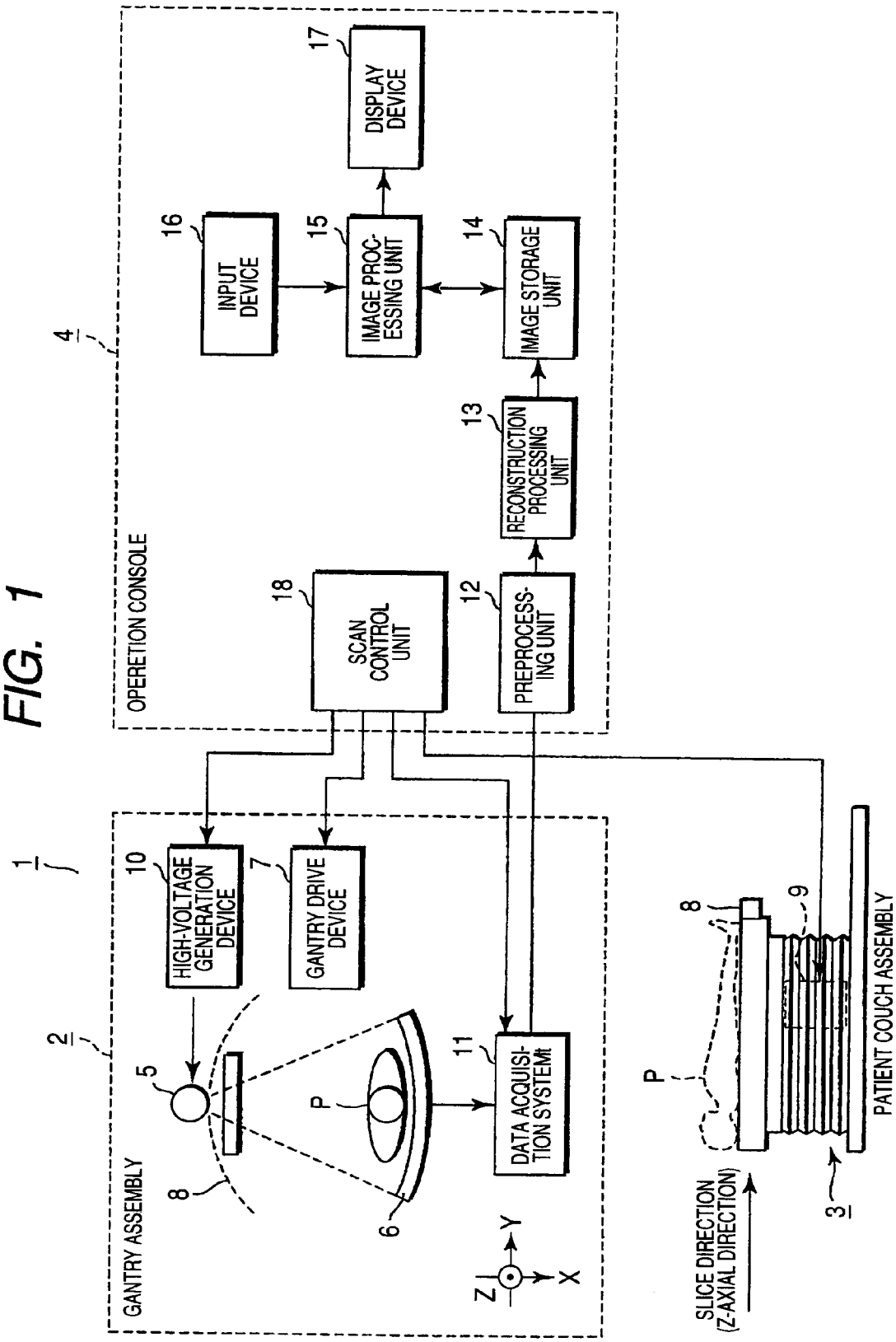
FIG. 1 is a block diagram of an X-ray CT apparatus according to the present invention.

FIG. 1 is a block diagram of an X-ray CT apparatus according to the first embodiment. The X-ray CT apparatus 1 includes a gantry 2 which is configured in order to acquire projection data on a patient, a patient couch 3 which serves to carry and move the patient P, and an operation console which serves to perform inputting and image display for operating the X-ray CT apparatus 1.

The gantry 1 has an X-ray tube 5 and an X-ray detector 6. The X-ray tube 5 and the X-ray detector 6 are mounted on a ring-shaped rotation frame 8 which is driven to rotate by a gantry drive device 7. The patient couch 3 includes a top 8 on which the patient is placed, and a top drive device 9 which serves to move the top 8. The rotation frame 8 has an opening at its central part. The patient P placed on the top 8 is inserted into the opening. Incidentally, the axis of the center of the rotation of the rotation frame 8 is defined by a Z-axis (the axis of a slice direction), and planes orthogonal to the Z-axis are defined by two orthogonal axes of X and Y.

A tube voltage is applied between the cathode and anode of the X-ray tube 5 by a high-voltage generator 10. A filament current is fed from the high-voltage generator 10 to the filament of the X-ray tube 5. X-rays are generated by the application of the tube voltage and the feed of the filament current. A unidimensional array type detector or a two-dimensional array type detector (also termed "multislice type detector") is adopted as the X-ray detector 6. An X-ray detection element has a light receiving face which is, for example, 0.5 mm×0.5 mm square. The X-ray detection elements numbering, for example, 916 are arrayed in a channel direction. Such arrays numbering, for example, 40 are juxtaposed in the slice direction, thereby to form the two-dimensional array type detector. A detector formed of the single array is the unidimensional array type detector.

A data acquisition system 11 is generally called "DAS" (Data Acquisition System). The data acquisition system 11 converts a signal outputted from the detector 6 every channel, into a voltage signal, and it amplifies the voltage signal and further converts this signal into a digital signal. Data (raw data) after the conversion are supplied to the operation console 4 outside the gantry.

The preprocessing unit 12 of the operation console 4 subjects the data (raw data) outputted from the data acquisition system 11, to the correction processes of a sensitivity correction etc., so as to output the projection data. The projection data are sent to a reconstruction processing unit 13. The reconstruction processing unit 13 reconstructs image data on the basis of the projection data acquired by, for example, helical scan or/and volume scan using cone beam X-rays, and it stores the image data in an image storage unit 14. An image processing unit 15 generates a display image on the basis of the image data stored in the image storage unit 14. The settings of conditions for displaying the image, the setting of a region of interest, etc. are performed on the basis of inputs to an input device 16 by an operator. The details of the image processing unit will be explained later. A display device 17 displays the image generated by the image processing unit 15. Besides, the scan control unit 18 of the operation console 4 controls the high-voltage generation device 10, gantry drive device 7, data acquisition system 11 and top drive device 9 so that the scan such as helical scan may be performed on the basis of the inputs of the operator. Incidentally, the operation console 4 may be configured of dedicated hardware, or the same functions may well be incarnated by software by employing a computer.

Figure 2:
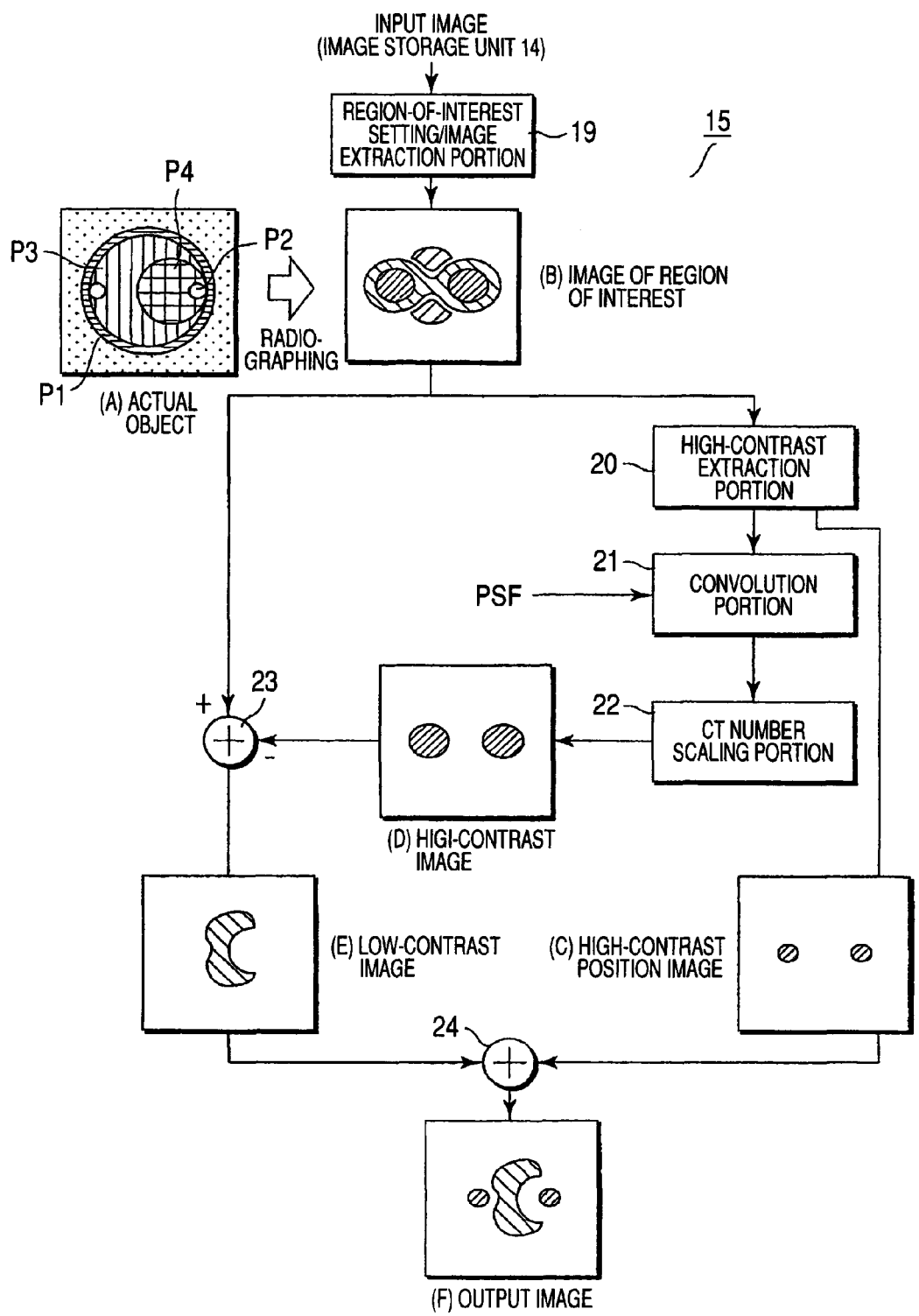
FIG. 2 is a block diagram of an image processing unit according to the first embodiment of the invention.
Figure 3:
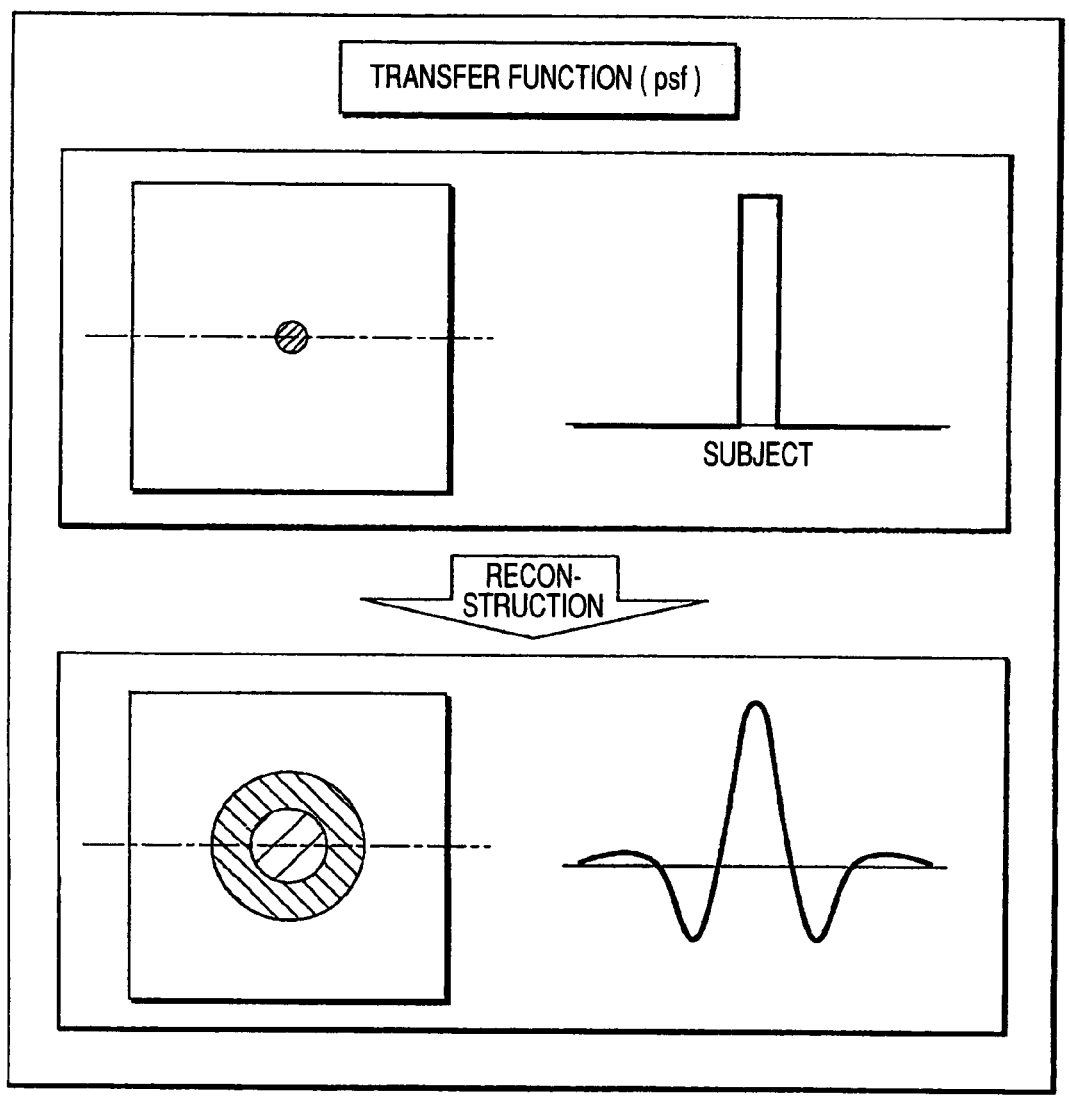
FIG. 3 is an explanatory diagram of a propagation speed function.

FIG. 2 is a diagram for explaining the configuration of the image processing unit 15 in FIG. 1. Incidentally, (A) in FIG. 2 is a model diagram of a blood-vessel sectional structure which is one example of a subject for image processing. The sectional structure contains a vascular wall P1, a stent P2, a contrast medium (blood flow part) P3, and lipide P4. A case where the image of such an actual object has been processed, will be described as an example below.

The image processing unit 15 includes a region-of-interest setting/image extraction portion 19, a high-contrast extraction portion 20, a convolution portion 21, a CT number scaling portion 22, a subtractor 23, and an adder 24.

The region-of-interest setting/image extraction portion 19 sets the region of interest on the basis of the input to the input device 16, and it extracts the image data of the region of interest from the image storage unit 14 and outputs the extracted image data. (B) in FIG. 2 represents the image of the region of interest as extracted by the region-of-interest setting/image extraction portion 19.

The high-contrast extraction portion 20 extracts a high-contrast region of very high X-ray attenuation coefficient, that is, a group of pixels having very high CT numbers, from the image of the region of interest as extracted by the extraction portion 19. As high-contrast substances, there are metallic instruments such as the stent which is embedded in the patient for the purpose of medical care, calcified calcium, and so forth. Incidentally, as a high-contrast substance in a low-contrast image except the stent etc. to be stated later, a subject to be chiefly handled is not the stent or the like, but it is the contrast medium. The contrast medium which has a CT number between those of the stent and the vascular wall is selectively used.

As a practicable extraction process, a binarized image is obtained in such a way that the difference between the value of a noted pixel and the mean value of the values of a plurality of pixels around the noted pixel is evaluated, thereby to obtain the differential image of the inputted image, and that the differential image is subjected to a threshold value process by employing a threshold value which corresponds to the peripheral edge of the stent. The binarized image becomes an image in which pixel values differ between a part where the high-contrast substance will exist and the other part. That is, the binarized image becomes an image which contains the information of positions where the high-contrast substance will exist (hereinbelow, termed "high-contrast position image"). (C) in FIG. 2 represents the high-contrast position image. In the differentiation/binarization process, the high-contrast position image can be easily obtained by a comparatively small number of arithmetic processes.

The convolution portion 21 subjects the high-contrast position image to the convolution calculation of a point spread function (PSF) peculiar to the pertinent X-ray computer-tomographic apparatus. The PSF is also called "transfer function" or "unsharpness function" as a function which defines an unsharpness characteristic peculiar to the apparatus. The PSF is obtained as the data of a two-dimensional image (unsharp image) concerning a wire phantom as has been obtained in such a way that the wire phantom which is more minute than the detector pitch (resolution limit) of the detector 6, for example, 0.5 mm and which has a diameter (0.05 mm) of, for example, 1/10 of the detector pitch is scanned, and that the two-dimensional image is reconstructed from the projection data of the scan. An image which is reconstructed from data acquired by scanning the high-contrast subject singly, that is, an image which contains the high-contrast subject and unsharpness appearing in the surroundings thereof, is obtained by convoluting the PSF into the high-contrast position image.

The CT number scaling portion 22 normalizes (scales) the image (unsharp image) outputted from the convolution portion 21, in accordance with a value which is not unique as a CT number, here, a CT number which is standard for the contrast medium. The normalization process is the level adjustment process of pixel values for a subtraction process to be explained below. (D) in FIG. 2 represents an image which is outputted from the CT number scaling portion 22 (hereinbelow, termed "high-contrast image").

The subtractor 23 executes the subtraction process, and obtains the difference image between the image of the region of interest and the high-contrast image. Thus, there is obtained a low-contrast image in which the unsharp components of the high-contrast substance and the surroundings thereof are relieved from the image of the region of interest. The low-contrast image is an image which represents a substance of low attenuation coefficient. (E) in FIG. 2 represents the low-contrast image.

The adder 24 adds the high-contrast position image to the low-contrast image, thereby to add the position information of the high-contrast substance. (F) in FIG. 2 represents the resulting output image. The output image is such that the position information of the high-contrast substance has been added to the image in which the unsharpness (artifact) ascribable to the high-contrast substance has been relieved from the original image of the region of interest, and it is displayed on the display device 17 via the processing of the succeeding stage. In the output image, the lipide in the surroundings of the high-contrast substance as has been difficult of identification under the influence of the unsharpness in the original image can be favorably observed.

According to the first embodiment as described above, the unsharp components which appear in the surroundings of the high-contrast substance can be relieved, so that substances surrounding the high-contrast substance can be favorably observed. Especially in a case where the stent or calcification exists in a fine blood vessel having a diameter of 3 mm to 5 mm, such as the coronary artery of the heart, it is possible to favorably observe the vascular wall, the accumulated state of the lipide, the state of the contrast medium, etc. in the surroundings of the stent or calcification.

The first embodiment may well be variously modified and carried out. By way of example, although the high-contrast position image has been added in the embodiment, only the low-contrast image may well be displayed without executing the addition. It is also allowed to superpose and display marks of different color as indicate the positions of the high-contrast substance.

Further, although the X-ray CT apparatus has been described in the embodiment, the embodiment may well be carried out as a medical image processing apparatus which displays an image on the basis of the projection data, a CT image or the like outputted from the X-ray CT apparatus. Further, although the processing of the two-dimensional image has been described in the embodiment, the processing of a three-dimensional image may well be executed by subjecting a plurality of two-dimensional images to the above processing.

Further, the case where the pixel values of the image are the CT numbers has been described in the embodiment, but any values other than the CT numbers may well be used as long as they represent X-ray attenuation coefficients. Besides, although the high-contrast position image has been obtained by the differentiation/binarization process in the embodiment, it is also allowed to employ a method wherein a high-contrast position image is obtained by inversely convoluting a transfer function representative of unsharpness ascribable to a high-contrast substance, into an image, a method wherein the information items of the position and shape of a stent are stored beforehand, so as to obtain positional information on the basis of the stored information items, or the like.

Second Embodiment

Now, the second embodiment of the invention will be described. Incidentally, the same parts as in the first embodiment shall be omitted from description.

The second embodiment consists in that similar substances in an image are automatically classified by a clustering process in order to facilitate identifying the similar substances. It is known under ideal conditions that a plaque or lipide exhibits a CT number of −100 to 50, that a vascular wall exhibits a CT number of 50 to 129, and that a contrast medium contained in a blood flow exhibits a CT number of 130 to 350. In an actual examination, however, the CT numbers fluctuate under the influences of the body build of a patient, beam hardening, a reconstruction function, the sizes of the substances, the states of substances outside a region of interest, the concentration of the contrast medium, etc. In a method which performs regional extraction (regional division), such fluctuations of the CT numbers cannot be coped with, and the substances cannot be favorably classified. In this embodiment, a region A corresponding chiefly to the plaque, a region B corresponding chiefly to the vascular wall, and a region C corresponding chiefly to the contrast medium are extracted from a low-contrast image at a high precision.

Figure 4:
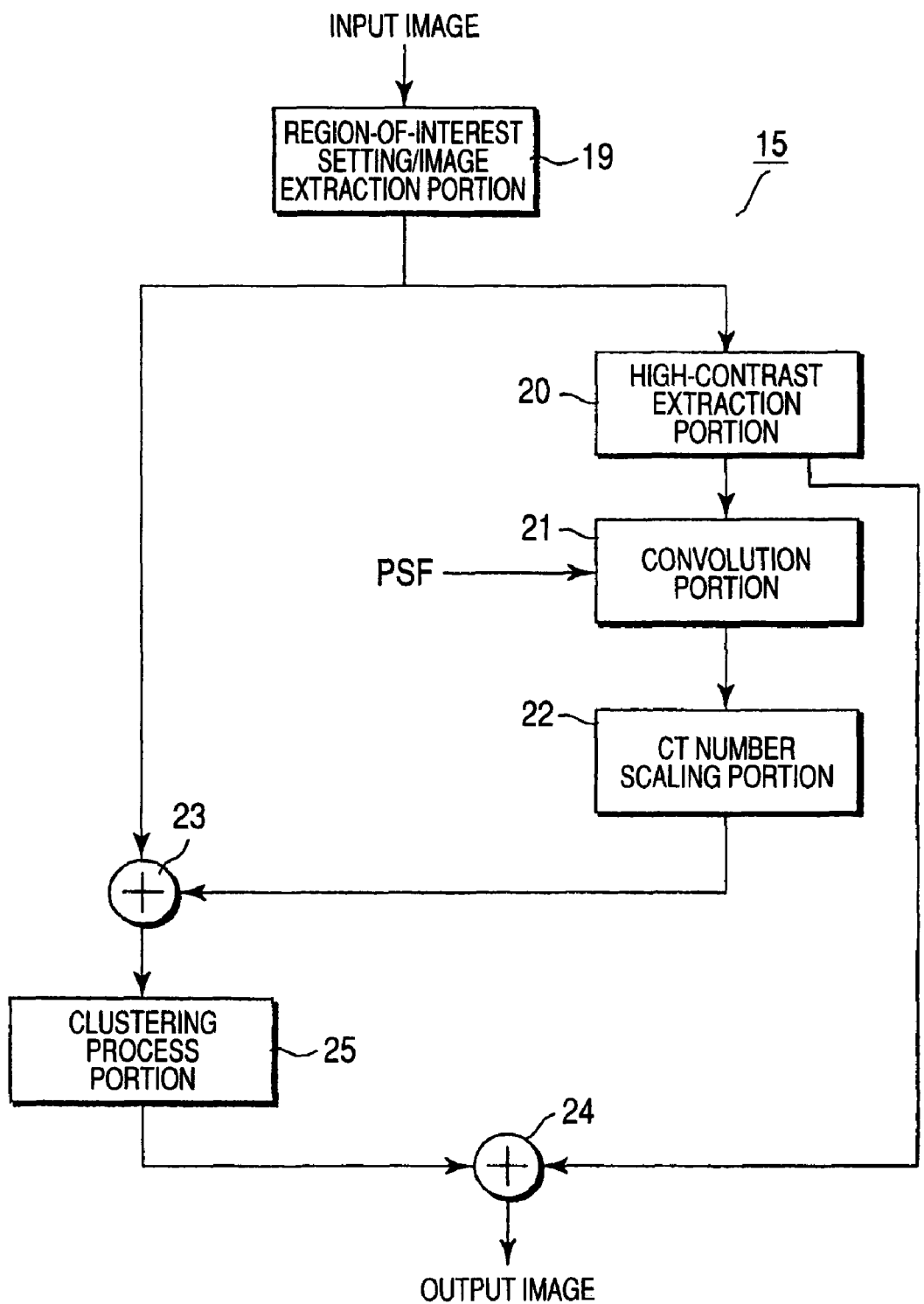
FIG. 4 is a block diagram of an image processing unit according to the second embodiment of the invention.

FIG. 4 is a block diagram of an X-ray CT apparatus 1 according to the second embodiment. In FIG. 4, a clustering process portion 25 is located between a subtractor 23 and an adder 24. The clustering process portion 25 finds a plurality of predetermined regions on the basis of CT numbers, and it executes the conversion processing of the CT numbers so that the individual regions may be indicated at or in the same intensity or color. Incidentally, a case where the CT numbers are divided into those of three regions will be described in this embodiment, but the number of regions may well be another number. Besides, the number of regions may well be made alterable in accordance with the input of an operator.

Figure 5:
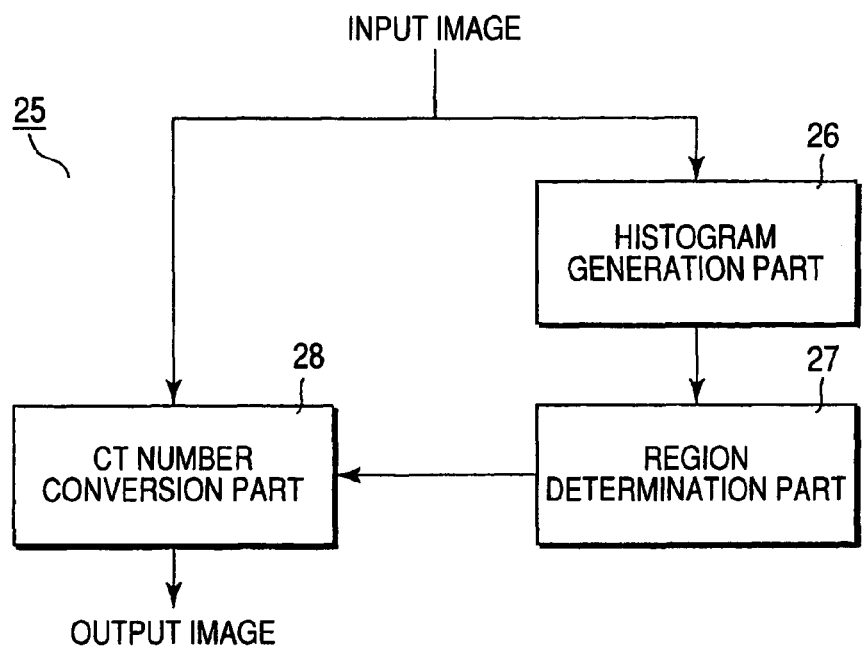
FIG. 5 is a block diagram of a clustering process portion according to the second embodiment of the invention.

FIG. 5 is a block diagram of the clustering process portion 25. The clustering process portion 25 includes a histogram generation part 26, a region determination part 27, and a CT number conversion part 28. The histogram generation portion 26 obtains the histogram of the inputted low-contrast image. The histogram represents the frequency distribution of pixel appearances at the respective CT numbers. Here, the CT numbers are distributed in the range between −100 and 537.

Figure 6:
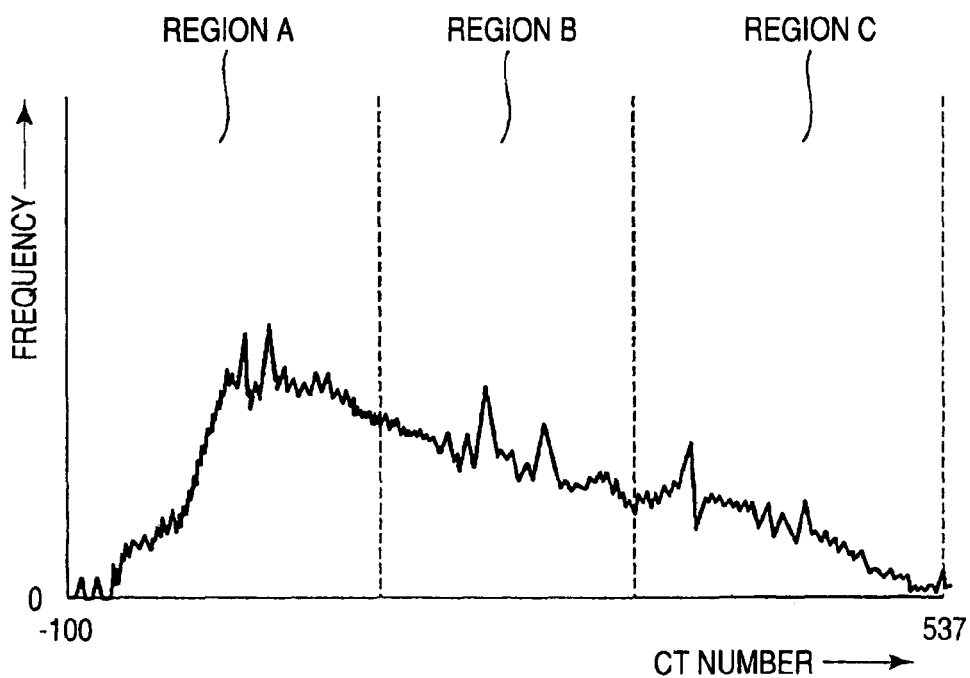
FIG. 6 is a graph showing three regions which are extracted by a clustering process.

As shown in FIG. 6, the region determination part 27 extracts, for example, three regions A, B and C from the low-contrast image. The region A corresponds chiefly to the plaque, and the region B corresponds chiefly to the vascular wall. The region C corresponds chiefly to the contrast medium.

Figure 7:
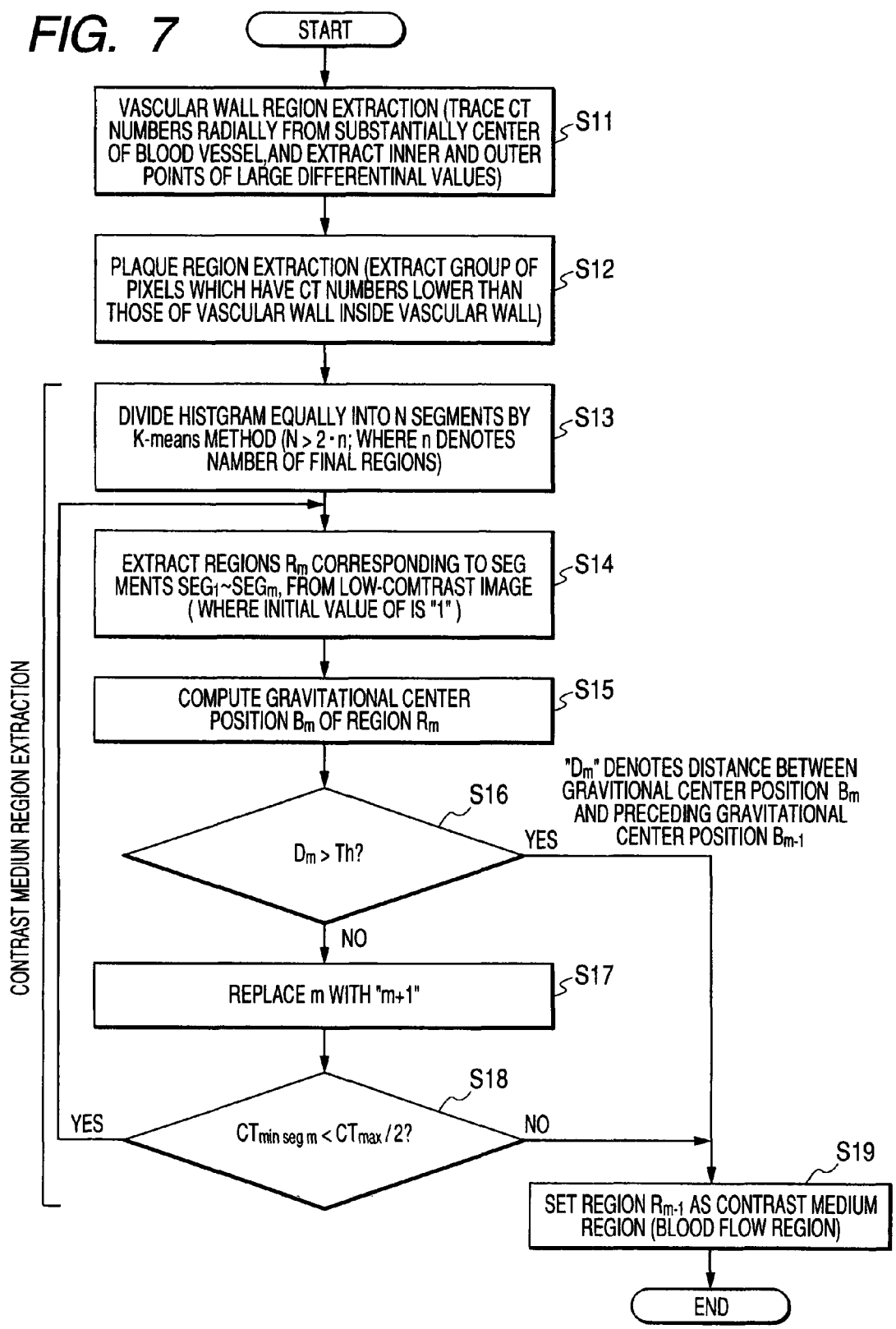
FIG. 7 is a flow chart showing the procedure of a region determination process which is based on a region determination part in FIG. 5.

FIG. 7 shows the procedure of a process in which the three regions A, B and C are extracted from the low-contrast image by the region determination part 27. First, the vascular wall region B is extracted from the low-contrast image (S11). A plurality of trace lines are set so as to be radial from substantially the center of a blood vessel designated by the operator. CT numbers are traced along the respective trace lines. Positions at which the fluctuations of the CT numbers are comparatively large, that is, two positions which exhibit differential values exceeding a predetermined value, are specified as the inner point and outer point of the vascular wall. Subsequently, the plaque region A is extracted from the low-contrast image (S12). A group of pixels which have CT numbers lower than those of the vascular wall inside the vascular wall, are extracted as the plaque region A.

Figure 8:
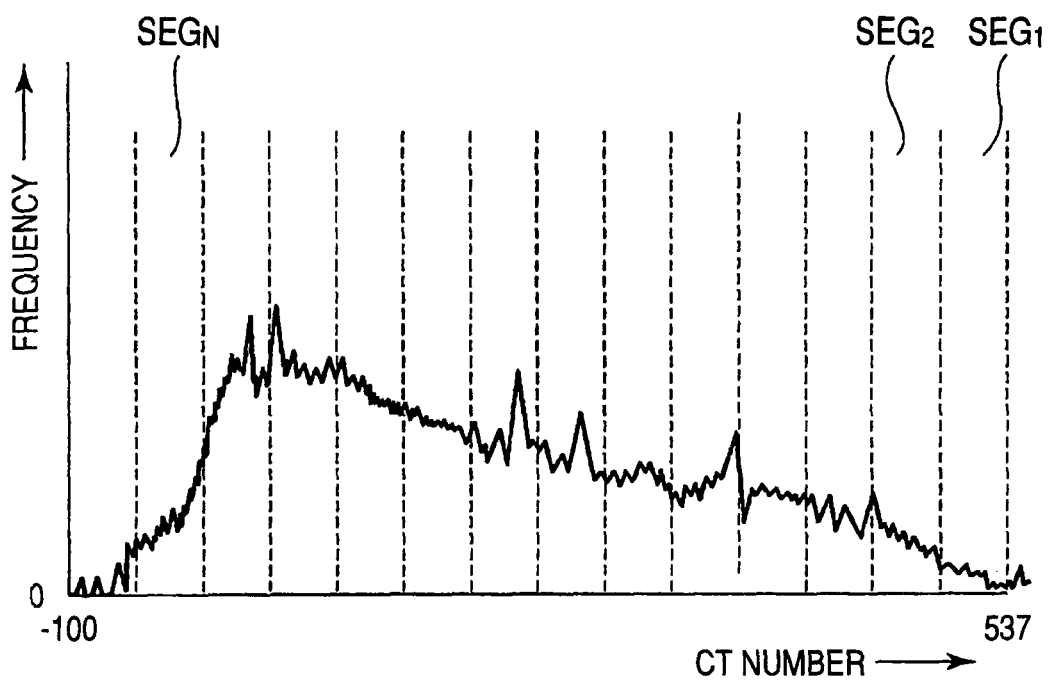
FIG. 8 is a supplementary graph of a step S13 in FIG. 7.

Subsequently, the region C of the contrast medium is extracted (S13-S19). First, as exemplified in FIG. 8, the range in which the CT numbers are distributed on the histogram (in FIG. 6, the range of from −100 to 537) is divided into N segments $SEG_1$-$SEG_N$ by the k-means method (S13). The segment of the highest CT number is set as $SEG_1$. "N" is set at an integer which exceeds the number n of the regions that are to be finally classified (here, n=3). Preferably, "N" is set to be double or triple the number n of the regions which are to be finally classified. "m" denotes a processing variable. The variable "m" is initialized to "1".

Figure 9:
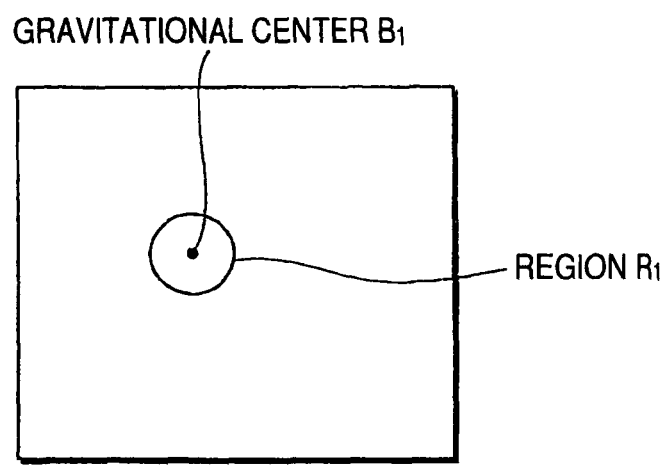
FIG. 9 is a diagram showing a region R1 extracted at a step S14 in FIG. 7, and a gravitational center position B1 computed at a step S15.

First, as shown in FIG. 9, a region candidate $R_1$ corresponding to the segment $SEG_1$ is extracted from the low-contrast image (S14). The region $R_1$ is extracted from the low-contrast image by setting the lowest value of the segment $SEG_1$ as a threshold value. The gravitational center position $B_1$ of the extracted region candidate $R_1$ is computed (S15). At the step S17, the variable m is incremented one (S17). Incidentally, at the step S18, "$\overline{CT}_{min}$ seg m<$CT_{max}/2$" is judged as a stop condition for preventing diffusion. "$CT_{min}$ seg m" denotes the minimum number of the segment m, while "$CT_{max}/2$" denotes the maximum CT number of the low-contrast image. More specifically, when the minimum number of the segment m is less than ½ of the maximum CT number of the low-contrast image, regional expansion processing is stopped. When the step S18 results in "No", the step S19 is executed. When the step S18 results in "Yes", the extraction process returns to the step S14.

Figure 10:
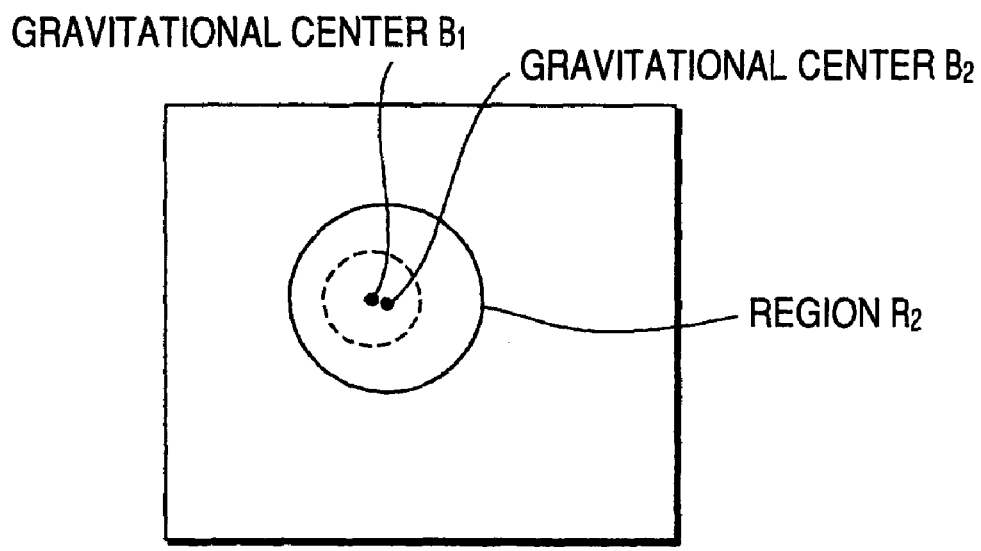
FIG. 10 is a diagram showing a region R2 extracted at the step S14 in FIG. 7, and a gravitational center position B2 computed at the step S15.

As shown in FIG. 10, a region candidate $R_2$ corresponding to the segment $SEG_1$ and segment $SEG_2$ is extracted from the low-contrast image (S14). In actuality, the region candidate $R_2$ is extracted from the low-contrast image by setting the lowest value of the segment $SEG_2$ as a threshold value. The gravitational center position $B_2$ of the extracted region candidate $R_2$ is computed (S15). The distance $D_2$ between the gravitational center position $B_2$ of the region candidate $R_2$ and the gravitational center position $B_1$ of the last region candidate $R_1$ is computed, and it is compared with a predetermined threshold value "Th" (S16).

The processing of the steps S14-S18 is looped until the displacement magnitude D of the gravitational center position exceeds the threshold value Th. That is, the region candidate R is expanded little by little in accordance with the increment of the variable m. As the region candidate R is expanded, the gravitational center B is displaced. When a subject for the extraction is the same, the displacement magnitude of the gravitational center B is comparatively small. When the subject for the extraction has been expanded so as to contain another substance, the displacement magnitude of the gravitational center B becomes comparatively large. More specifically, when the subject for the extraction is the contrast medium, the gravitational center position does not change very much in spite of the expansion of the region candidate R. However, when the vascular wall or the like has been added to the subject for the extraction, the region candidate R rapidly becomes large, and also the gravitational center position changes greatly. A segment in which the gravitational center position changes greatly, is searched for.

Figure 11:
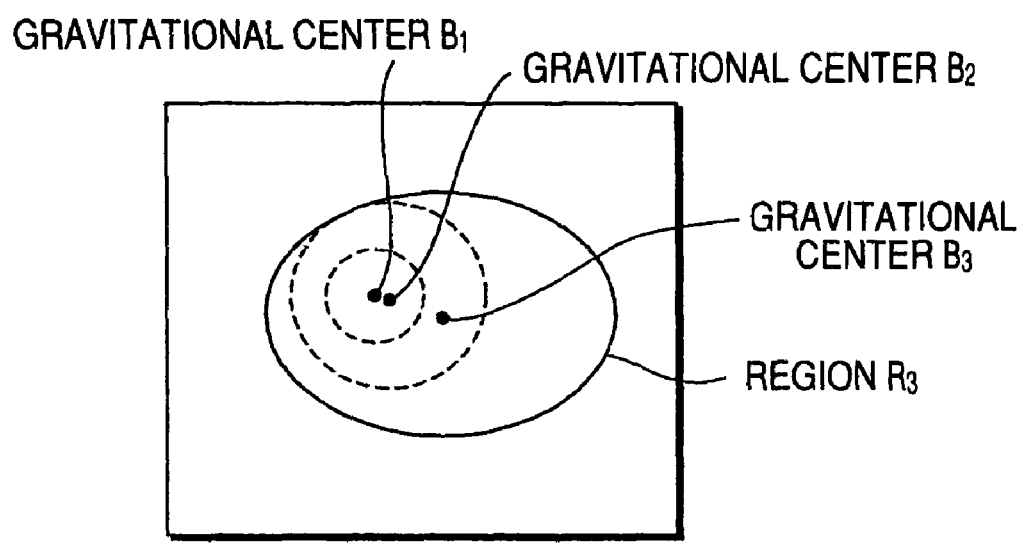
FIG. 11 is a diagram showing a region R3 extracted at the step S14 in FIG. 7, and a gravitational center position B3 computed at the step S15.

When, as shown in FIG. 11, the distance $D_3$ between the gravitational center position $B_3$ of the region candidate $R_3$ and the gravitational center position $B_2$ of the last region candidate $R_2$ has exceeded the threshold value Th at m=3 (S16), the last region candidate $R_2$ is specified as the region C of the contrast medium (S19). That is, the largest region candidate $R_2$ in which the displacement magnitude of the gravitational center is less than the threshold value Th is selected as the specified region C.

In this manner, note is taken of the displacement of the gravitational center position based on the regional expansion, whereby the region C of the contrast medium can be extracted at a high precision without being considerably influenced by the factors of the CT number fluctuations. Besides, regarding the vascular wall extraction, the region B of the vascular wall can be similarly extracted at a high precision without being considerably influenced by the factors of the CT number fluctuations, by taking note of the CT number change. Further, regarding the plaque extraction, the region A of the plaque can be similarly extracted at a high precision without being considerably influenced by the factors of the CT number fluctuations, by setting the condition of the CT numbers inside the vascular wall.

Incidentally, the region determination part 27 may well classify the histogram into three regions by employing the k-mean method. A threshold value "Th" for determining the individual regions is calculated by the k-mean method so that the variance values of CT numbers in the respective regions may become equal. The respective regions are determined so that the variance values of the CT numbers in the respective regions may become equal, whereby substances of high similarities are easily included in the same region.

FIG. 6 represents the example in which the regions are divided by this embodiment, and the CT numbers of −100 to 537 are classified into the three regions. Pixels having the CT numbers in the range of the region A correspond chiefly to the part of the lipide. Pixels having the CT numbers in the range of the region B correspond chiefly to the part of the vascular wall. Pixels having the CT numbers in the range of the region C correspond chiefly to the part of the plaque.

The CT number conversion part 28 replaces the CT numbers of the pixels respectively included in the three regions extracted or classified by the region determination part 27, with the characteristic values of the respective regions as have been set beforehand. Thus, the same regional part is displayed at or in the same intensity or color on a display image, and the respective regions are displayed in graspable aspects.

According to this embodiment as described above, the image in which the regions are divided in accordance with the CT numbers is displayed, and it is therefore possible to provide an image from which different substances such as a tissue, the lipide and the contrast medium within the patient can be favorably grasped. Besides, since the threshold values for determining the regions are automatically found on the basis of the histogram, it is possible to provide an image in which the regions are favorably classified even in the existence of the fluctuations of CT numbers.

Besides, in this embodiment, the low-contrast image is subjected to the clustering process after the unsharp components (artifact components) appearing in the surroundings of the high-contrast substances have been relieved, so that substances in the surroundings of the high-contrast substances can be favorably observed. Especially in a case where a stent or calcification exists in a fine blood vessel having a diameter of 3 mm to 5 mm, such as the coronary artery of the heart, it is possible to favorably observe the vascular wall, the accumulated state of the lipide, the state of the contrast medium, etc. in the surroundings of the stent or calcification.

Besides, the clustering process is executed for the image in which the high-contrast substances are not contained, and the information items of the high-contrast substances are thereafter added, so that the regional division of a part having low CT numbers can be favorably made.

Incidentally, the invention is not restricted to the embodiments, but it can be concretized by modifying the constituents within a scope not departing from the purport thereof, at the stage of performance. Besides, various inventions can be formed by appropriately combining two or more of the constituents disclosed in the embodiments. By way of example, several constituents may well be omitted from all the constituents indicated in each embodiment. Further, the constituents in the different embodiments may well be appropriately combined.

By way of example, although the threshold values have been calculated by the k-mean method in the above embodiment, they may well be calculated by employing another clustering technique such as the group mean method or the Ward method. Besides, in the above embodiment, the clustering process has been executed for the image in which the high-contrast substance and the unsharpness in the surroundings thereof have been eliminated, but a display image may well be generated by executing a clustering process directly for the original image of the region of interest, without executing the such a process of the embodiment.

Further, although the high-contrast position image has been added in each embodiment, only the low-contrast image may well be displayed without the addition. Besides, a mark of different color as indicates the position of the high-contrast substance may well be displayed in superposition.

Further, although the X-ray CT apparatus has been described in the above embodiment, the embodiment may well be carried out as a medical image processing apparatus which displays an image on the basis of the projection data, a CT image or the like outputted from the X-ray CT apparatus. Further, although the processing of the two-dimensional image has been described in the above embodiment, the processing of a three-dimensional image may well be executed by subjecting a plurality of two-dimensional images to the above processing. Further, the case where the pixel values of the image are the CT numbers has been described in the above embodiment, but any values other than the CT numbers may well be used as long as they represent X-ray attenuation coefficients.

According to the present invention, in case of displaying an X-ray absorption distribution image within a patient as has been obtained by an X-ray CT apparatus, unsharpness which appears in the surroundings of an object of high X-ray attenuation coefficient can be relieved.

What is claimed is:

1. An X-ray CT apparatus wherein projection data on a patient are acquired, and an original image of the patient is reconstructed based on the acquired projection data, the X-ray CT apparatus comprising:
    a high contrast extraction unit configured to extract a high-contrast region having a comparatively high X-ray attenuation coefficient from the original image;
    a convolution unit configured to generate an unsharp image concerning the high-contrast region based on a position of the extracted high-contrast region and a point spread function peculiar to the CT apparatus, wherein said convolution unit includes a unit configured to convolute the point spread function into a position image of the extracted high-contrast region, and a unit configured to normalize the convoluted position image of the high-contrast region in accordance with a standard CT number of the high-contrast region; and
    a unit which configured to subtract the unsharp image from the original image to generate a low-contrast image concerning a low-contrast region of comparatively low X-ray attenuation coefficient.

2. The X-ray CT apparatus as defined in claim 1, wherein said high contrast extraction unit is configured to extract the high-contrast region by generating a differential image from the original image, and subjecting the differential image to threshold processing.

3. The X-ray CT apparatus as defined in claim 1, wherein the high contrast extraction region is configured to extract the high-contrast region, which is a metallic instrument embedded in the patient for medical treatment, or calcified calcium.

4. The X-ray CT apparatus as defined in claim 1, further comprising a unit configured to add a position image of the extracted high-contrast region to the low-contrast image.

5. The X-ray CT apparatus as defined in claim 1, further comprising:
    a classification unit configured to classify the low-contrast image into a plurality of regions in accordance with CT numbers; and
    a unit configured to replace pixel values of the low-contrast image with values that are respectively peculiar to the plurality of classified regions.

6. The X-ray CT apparatus as defined in claim 5, further comprising a unit configured to add a position image of the extracted high-contrast region to the replaced low-contrast image.

7. The X-ray CT apparatus as defined in claim 5, wherein the classification unit is configured to classify the low-contrast image into the plurality of regions including a region in which lipide is predominant, a region in which a vascular wall is predominant, and a region in which a contrast medium is predominant.

8. The X-ray CT apparatus as defined in claim 5, wherein the classification unit includes:
    a unit configured to extract a plurality of regions of different sizes from the low-contrast image on the basis of a plurality of threshold values;
    a unit configured to compute respective gravitational centers of the plurality of extracted regions; and
    a unit configured to select a specified region corresponding to a subject for the extraction, from the plurality of extracted regions on the basis of distances between the gravitational centers.

9. The X-ray CT apparatus as defined in claim 8, wherein the plurality of threshold values are determined based on a frequency distribution of pixel appearances of the respective CT numbers concerning the image.

10. An X-ray CT apparatus wherein projection data on a patient are acquired, and an original image within the patient is reconstructed based on the acquired projection data, the X-ray CT apparatus comprising:
    a convolution unit configured to generate an unsharp image concerning a high-contrast region having a comparatively high X-ray attenuation coefficient in the original image based on a position of the extracted high-contrast region and a point spread function peculiar to the CT apparatus, wherein said convolution unit includes a unit configured to convolute the point spread function into a position image of the high-contrast region, and a unit configured to normalize the convoluted position image of the high-contrast region in accordance with a standard CT number of the high-contrast region;
    a unit configured to subtract the unsharp image concerning the high-contrast region contained in the original image, from the original image to generate a low-contrast image concerning a region of comparatively low X-ray attenuation coefficient;

a classification unit configured to classify the low-contrast image into a plurality of regions in accordance with CT numbers; and a unit configured to replace pixel values of the low-contrast image with values that are respectively peculiar to the plurality of classified regions.

11. The X-ray CT apparatus as defined in claim 10, wherein the classification unit is configured to classify the low-contrast image into a contrast medium region, a vascular wall region, and a plaque region.

12. The X-ray CT apparatus as defined in claim 11, wherein to identify the contrast medium region, said classification unit includes:

a unit configured to extract a plurality of included region candidates of different sizes in succession, from the low-contrast image based on the plurality of threshold values;

a unit configured to compute respective gravitational centers of the plurality of extracted regions; and a unit configured to select the contrast medium region from the plurality of extracted region candidates based on distances between the gravitational centers.

13. The X-ray CT apparatus as defined in claim 12, wherein the plurality of threshold values are determined based on a frequency distribution of pixel appearances of respective CT numbers concerning the image.

14. The X-ray CT apparatus as defined in claim 12, wherein the selection unit is configured to select a region in which a displacement magnitude of the gravitational center is the largest within a range less than a predetermined magnitude, as the specified region.

15. The X-ray CT apparatus as defined in claim 12, wherein to identify the vascular wall region, said classification unit is configured to trace the CT numbers radially from substantially a center of a blood vessel of the low-contrast image, and to specify two positions at which changes of the CT numbers exceed a predetermined value, as an inner wall and an outer wall of the blood vessel.

16. The X-ray CT apparatus as defined in claim 15, wherein to identify the plaque region, said classification unit is configured to extract a group of pixels having CT numbers lower than those of the vascular wall, inside the vascular wall.

17. In an X-ray CT apparatus wherein projection data on a patient are acquired, and an image within the patient is reconstructed on the basis of the acquired projection data, an X-ray CT apparatus comprising:

a unit which extracts a plurality of included region candidates of different sizes in succession, from an image on the basis of a plurality of threshold values;

a unit which computes respective gravitational centers of the plurality of extracted regions; and a unit which selects a specified region from the plurality of extracted region candidates on the basis of distances between the gravitational centers.

18. An X-ray CT apparatus as defined in claim 17, wherein the plurality of threshold values are determined on the basis of a frequency distribution of pixel appearances of respective CT numbers concerning the image.

19. An X-ray CT apparatus as defined in claim 17, wherein the selection unit selects a region in which a displacement magnitude of the gravitational center is the largest within a range less than a predetermined magnitude, as the specified region.

20. An image processing apparatus, comprising:

a high contrast extraction unit which is configured to extract a high-contrast region of having a comparatively high X-ray attenuation coefficient from an original X-ray image;

a convolution unit configured to generate an unsharp image concerning the high-contrast region based on a position of the extracted high-contrast region and a point spread function peculiar to the apparatus, wherein said convolution unit includes a unit configured to convolute the point spread function into a position image of the extracted high-contrast region, and a unit configured to normalize the convoluted position image of the high-contrast region in accordance with a standard CT number of the high-contrast region; and a unit configured to subtract the unsharp image from the original image to generate a low-contrast image concerning a low-contrast region of comparatively low X-ray attenuation coefficient.

21. An image processing apparatus, comprising:

a convolution unit configured to generate an unsharp image concerning a high-contrast region having a comparatively high X-ray attenuation coefficient in an original image based on a position of the high-contrast region and a point spread function peculiar to the CT apparatus, wherein said convolution unit includes a unit configured to convolute the point spread function into a position image of the high-contrast region, and a unit configured to normalize the convoluted position image of the high-contrast region in accordance with a standard CT number of the high-contrast region;

a unit configured to subtract the unsharp image concerning the high-contrast region contained in the original X-ray image, from the original X-ray image, and to generate a low-contrast image concerning a region of comparatively low X-ray attenuation coefficient;

a classification unit configured to classify the low-contrast image into a plurality of regions in accordance with pixel values; and a unit configured to replace the pixel values of the low-contrast image with values that are respectively peculiar to the plurality of classified regions.

22. An image processing apparatus, comprising:

a unit which extracts a plurality of included region candidates of different sizes in succession, from an X-ray image on the basis of a plurality of threshold values;

a unit which computes respective gravitational centers of the plurality of extracted regions; and a unit which selects a specified region from the plurality of extracted region candidates on the basis of distances between the gravitational centers.

* * * * *